United States Patent
Kamiguchi

(10) Patent No.: US 12,352,833 B2
(45) Date of Patent: Jul. 8, 2025

(54) MEDICAL DATA PROCESSING APPARATUS, MEDICAL DATA PROCESSING METHOD, AND MAGNETIC RESONANCE IMAGING APPARATUS

(71) Applicant: Canon Medical Systems Corporation, Otawara (JP)

(72) Inventor: Yuuzo Kamiguchi, Yokohama (JP)

(73) Assignee: Canon Medical Systems Corporation, Otawara (JP)

( * ) Notice: Subject to any disclaimer, the term of this patent is extended or adjusted under 35 U.S.C. 154(b) by 439 days.

(21) Appl. No.: 18/056,281

(22) Filed: Nov. 17, 2022

(65) Prior Publication Data

US 2023/0160982 A1   May 25, 2023

(30) Foreign Application Priority Data

Nov. 19, 2021   (JP) .................................. 2021-188912

(51) Int. Cl.
```
G01R 33/20      (2006.01)
A61B 5/055      (2006.01)
G01R 33/563     (2006.01)
```
(52) U.S. Cl.
CPC .............. *G01R 33/20* (2013.01); *A61B 5/055* (2013.01); *G01R 33/56341* (2013.01)

(58) Field of Classification Search
None
See application file for complete search history.

(56) References Cited

U.S. PATENT DOCUMENTS

2021/0003651 A1   1/2021  Kamiguchi

FOREIGN PATENT DOCUMENTS

JP   2021-010408 A   2/2021

OTHER PUBLICATIONS

Hamilton, "Measuring Cardiac Relaxation Times and Multi-Compartment Water Exchange With Magnetic Resonance Fingerprinting", May 2018, 190 pages.
Bjarnason et al., "Characterization of the NMR Behavior of White Matter in Bovine Brain", Magnetic Resonance in Medicine 54, 2005, 11 pages.

*Primary Examiner* — Lennin R Rodriguezgonzalez
*Assistant Examiner* — Lennin R Rodriguez
(74) *Attorney, Agent, or Firm* — Oblon, McClelland, Maier & Neustadt, L.L.P.

(57) ABSTRACT

According to one embodiment, a medical data processing apparatus includes processing circuitry. The processing circuitry acquires imaging data acquired by executing spoiled gradient echo imaging and coherent gradient echo imaging by using multiple flip angles. The processing circuitry generates a low-rank approximate image set, which is a set of low-rank approximated images from the imaging data. The processing circuitry reconstructs one or more parameter maps using the above low-rank approximate image set and a related to water exchange in a biological tissue, the multi-pool model including plural free waters and bound water that performs magnetization exchange with those free waters.

17 Claims, 16 Drawing Sheets

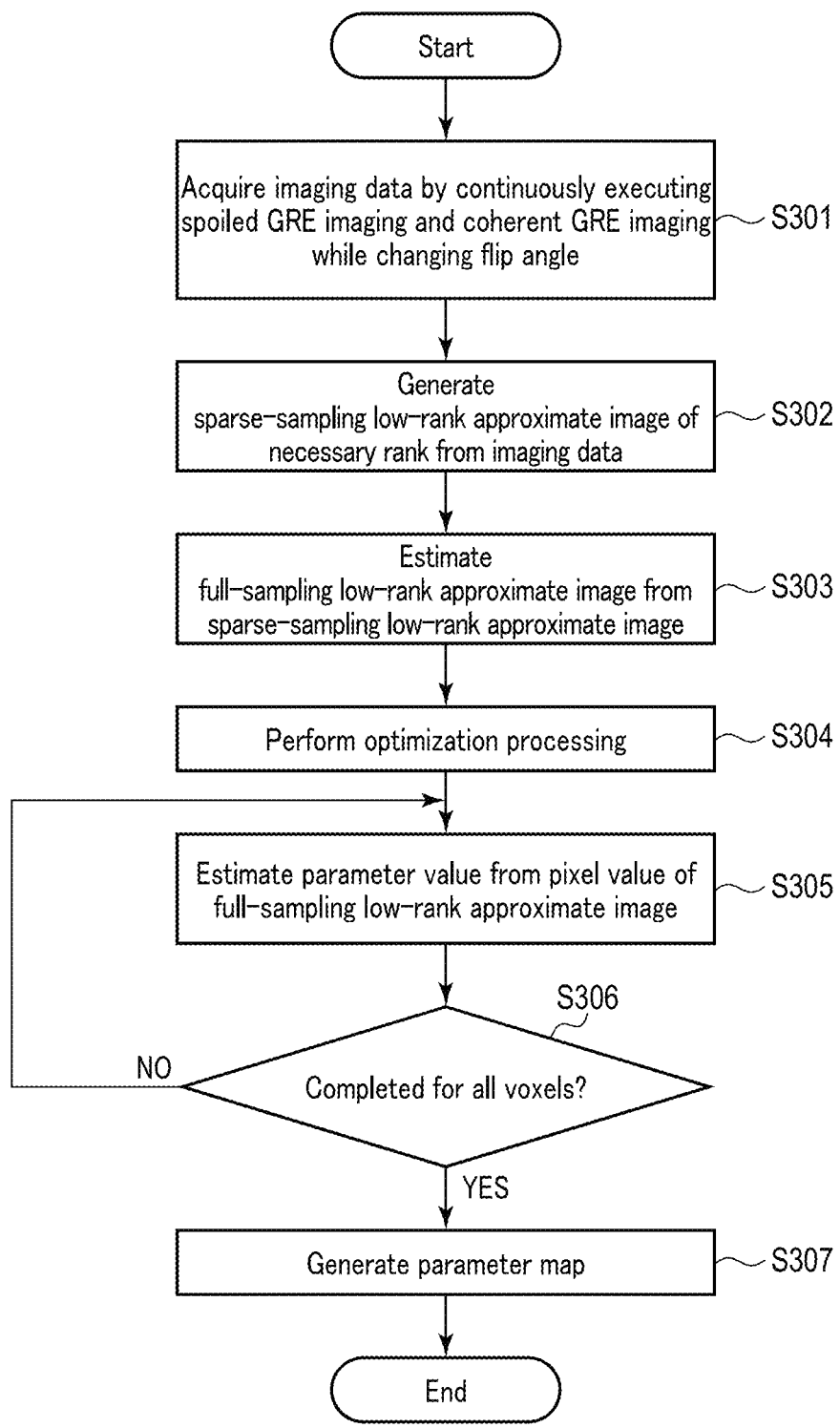
F I G. 3

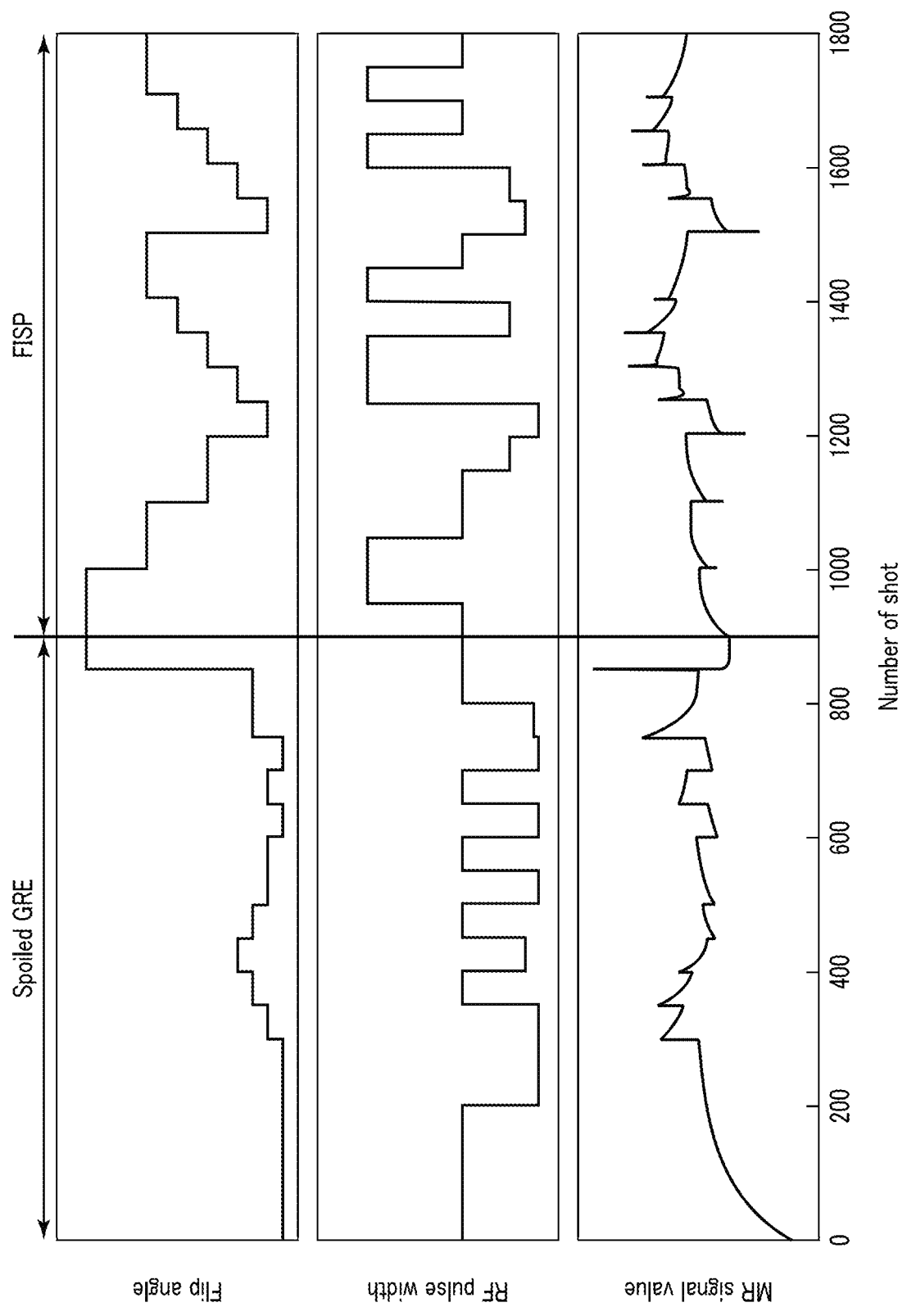
F I G. 5

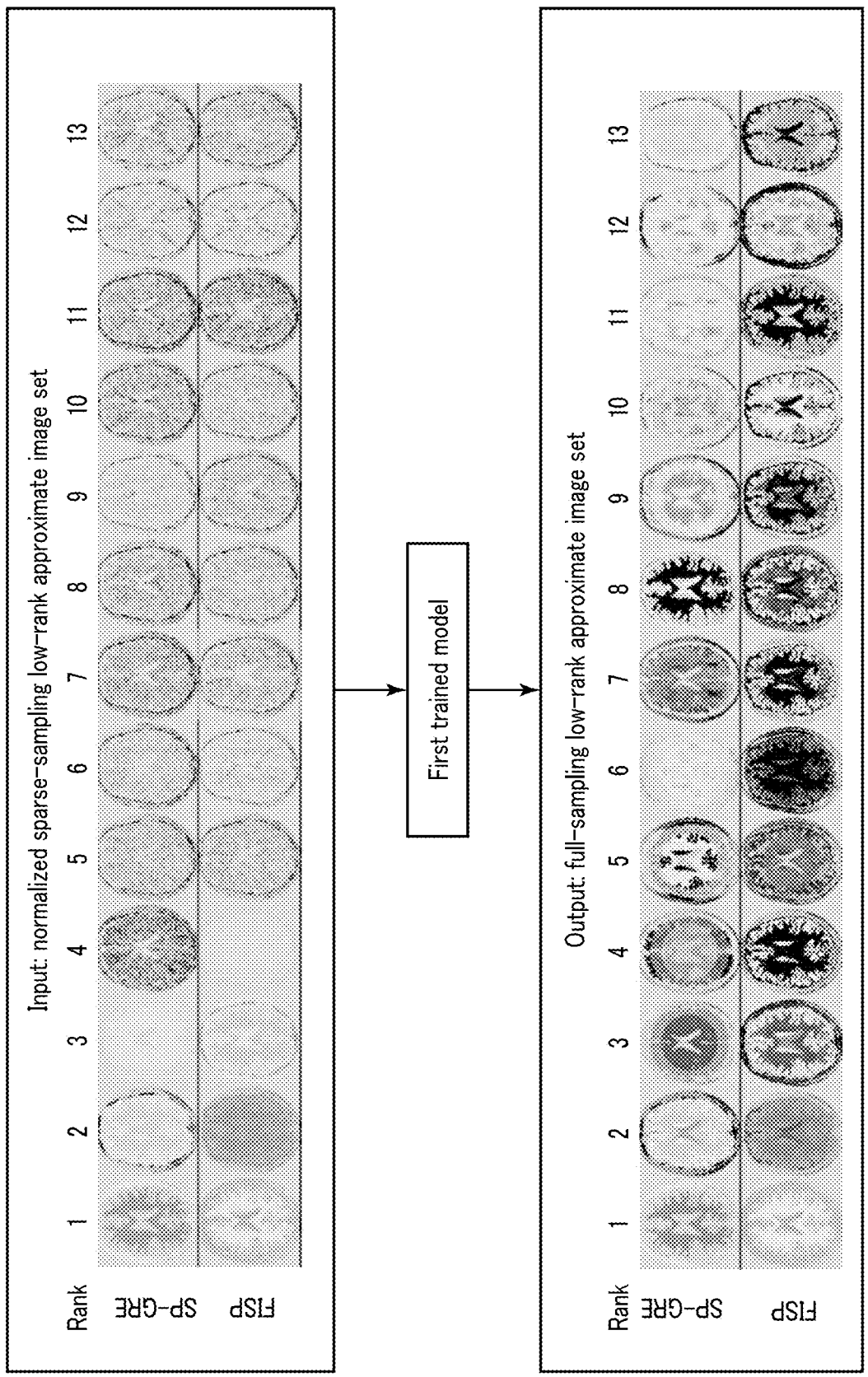
F I G. 10

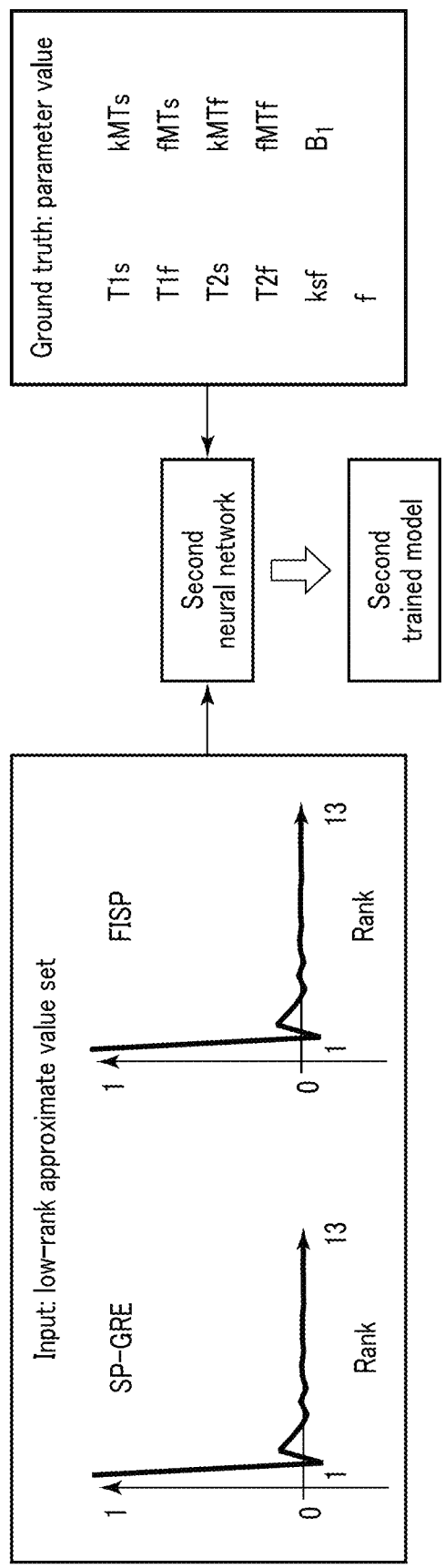
F I G. 12

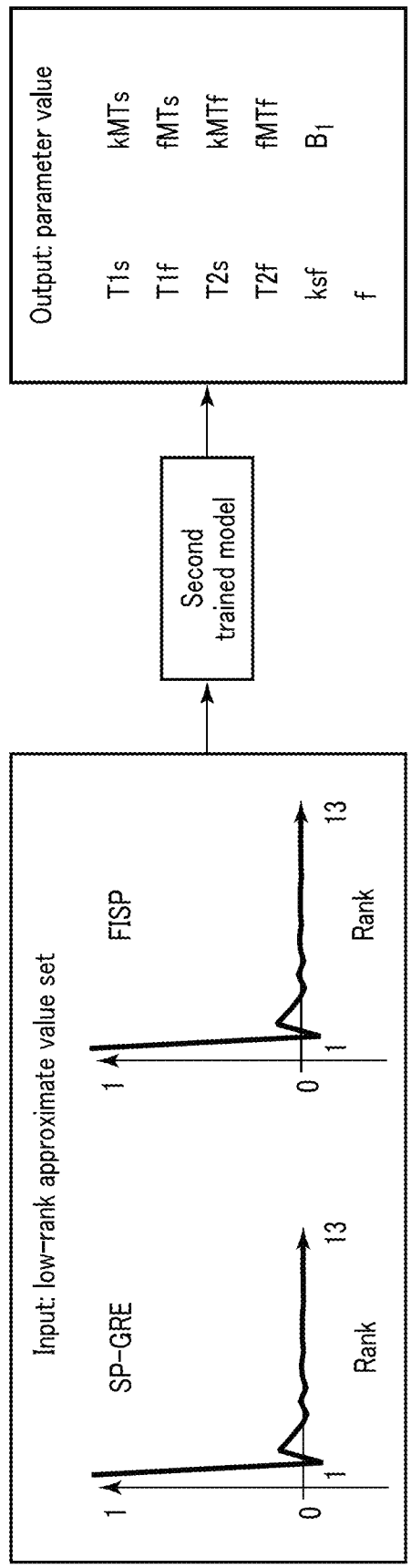
F I G. 13

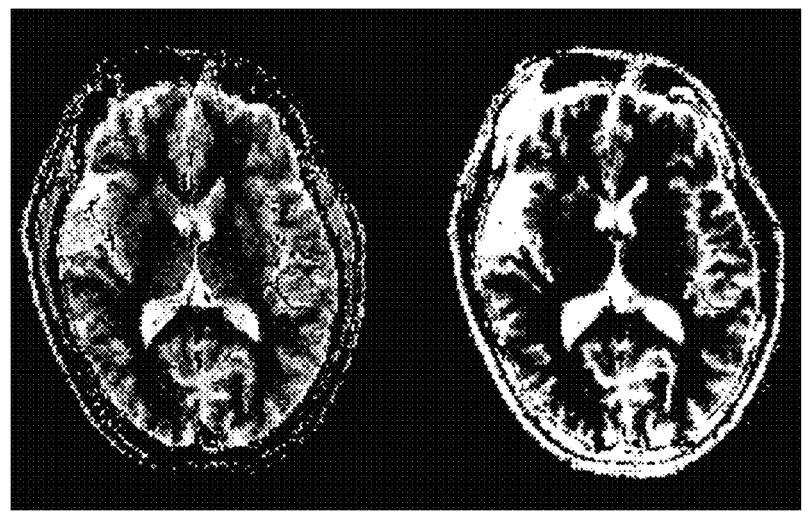
Generated IR-GRE T1 map    Generated CMPG T2 map
F I G. 16

MEDICAL DATA PROCESSING APPARATUS, MEDICAL DATA PROCESSING METHOD, AND MAGNETIC RESONANCE IMAGING APPARATUS

CROSS-REFERENCE TO RELATED APPLICATIONS

This application is based upon and claims the benefit of priority from Japanese Patent Application No. 2021-188912, filed Nov. 19, 2021, the entire contents of which are incorporated herein by reference.

FIELD

Embodiments described herein relate generally to a medical data processing apparatus, a medical data processing method, and a magnetic resonance imaging apparatus.

BACKGROUND

In the brain for example, depending on the structure of the biological tissue, there are two types of free water: free water that can move relatively freely, such as intracellular fluid and extracellular fluid, and free water that is restricted in movement, such as myelin water trapped in the myelin sheath. In the following, free waters having different characteristics are collectively referred to as plural free waters. The plural free waters perform water exchange mutually, and a ratio of existence of each free water also reflects the biological tissue structure.

There is a multi-compartment microstructure imaging technique that takes into account such parameters pertaining to the biological tissue structure. For example, there is a two-pool model that takes into account two types of free water. However, there is a problem wherein the two-pool model is inaccurate and unreliable because it does not take into account a magnetization transfer effect (MT effect) or $B_1$ distribution, and because it uses imaging data under a steady state.

Therefore, there is also a four-pool model, which is a multi-compartment microstructure model that takes the MT effect into account. However, the four-pool model has a large number of parameters, which is expected to take time to analyze, and it is unclear whether or not a quantitative value can be obtained for each parameter map, and imaging and analysis methods for imaging the parameter values are unknown.

BRIEF DESCRIPTION OF THE DRAWINGS

FIG. 3 is a flowchart showing an operation of the medical data processing apparatus according to the first embodiment.

FIG. 5 is a diagram showing another example of the imaging sequence according to the first embodiment.

FIG. 10 is a diagram showing an example of the first neural network at the time of inference (use).

FIG. 12 is a diagram showing an example of a second neural network at the time of training.

FIG. 13 is a diagram showing an example of the second neural network at the time of inference (use).

FIG. 16 is an example of another image based on a low-rank approximate value.

DETAILED DESCRIPTION

Figure 1:
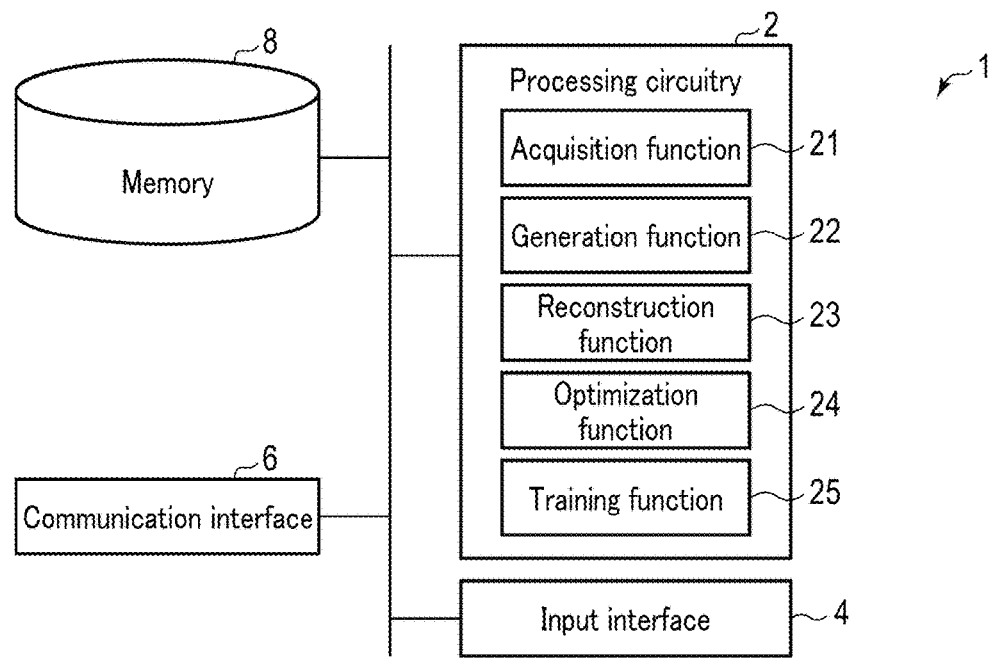
FIG. 1 is a block diagram showing a configuration of a medical data processing apparatus according to a first embodiment.

In general, according to one embodiment, a medical data processing apparatus includes processing circuitry. The processing circuitry acquires imaging data acquired by executing spoiled gradient echo imaging and coherent gradient echo imaging by using multiple flip angles. The processing circuitry generates a low-rank approximate image set, which is a set of low-rank approximated images from the imaging data. The processing circuitry reconstructs one or more parameter maps using the above low-rank approximate image set and a related to water exchange in a biological tissue, the multi-pool model including plural free waters and bound water that performs magnetization exchange with those free waters.

There is a two-pool model as a model that considers two types of free water.

The two types of water are referred to as a slow pool and a fast pool. A longitudinal relaxation time of the slow pool is defined as T1s [s] and a transverse relaxation time as T2s [s]. A longitudinal relaxation time of the fast pool is defined as T1f [s] and a transverse relaxation time as T2f [s]. A ratio of the fast pool to the total when the total is set to 1 is defined as "f". Thus, a ratio of the slow pool can be defined as "1−f". The slow and fast pools perform water exchange, and an exchange rate from the slow pool to the fast pool can be defined as ksf [Hz] and from the fast pool to the slow pool as kfs [Hz]. However, ksf and kfs have the following relationship from detailed balance conditions. Kfs·f=ksf·(1−f).

Therefore, the number of independent parameters in the two-pool model is 6. Separating and quantifying these parameters is useful for understanding a microstructure of a biological tissue and is known as a multicompartment microstructure imaging technique. Due to its technical difficulties, however, a quantitative value in current MRI (Magnetic Resonance Imaging) is generally obtained using a single-compartment model that assumes a single pool without separating plural waters (T1 map, T2 map, etc.).

However, since the analysis is based on a single-compartment model that differs from reality, it is an "apparent quantitative value" and depends on the imaging and analysis method, making it less versatile. In some cases, an error with a real biological model is so large that values obtained by other methods do not match, making comparisons with other methods or a combined analysis impossible.

Thus, it is desirable to execute multicompartment microstructure quantitative imaging, which is more consistent with reality, in order to obtain versatile quantitative parameters.

For example, mcDESPOT (multi-component driven equilibrium single pulse observation of T1 and T2) is known as a conventional high-speed imaging method for two-pool models. This is a method to execute imaging of SP-GRE (spoiled—gradient echo) and bSSFP (balanced steady state free precession) at different flip angles to obtain parameters of a two-pool model from steady-state signal values thereof.

However, since mcDESPOT does not take into account B1 distribution and a magnetization transfer (MT) effect, it is known that errors due to the B1 distribution and an on-resonance MT effect generated by excited RF cannot be ignored. When using bSSFP to obtain T2 information, the flip angle should be as large as possible to improve SNR and accuracy, but on the other hand, the MT effect becomes larger, so the MT effect cannot be ignored.

Another recent technique that has been proposed is the use of an MR fingerprinting imaging method to execute a two-pool model analysis. As the MR fingerprinting, a method has been proposed to execute FISP (fast imaging with steady precession) acquisition and matching with a dictionary of 2-pool models. However, the number of parameters can be as large as 6, so the dictionary can become huge, in which case dictionary matching takes time, and full-sampling imaging is required to obtain the necessary accuracy due to sparse artifacts during imaging. Thus, there is a problem wherein an imaging time, an analysis time, and an obtained accuracy are not at a practical level. Also, as with mcDESPOT above, there is the problem of ignoring the MT effect.

In reality, however, since the MT effect itself reflects the microstructure of the living body, it is desirable to be able to map the MT effect itself at the same time to obtain more detailed information about the biological tissue. In addition, taking the MT effect into account is desirable because it is expected to improve the agreement between reality and the model, as well as the accuracy, reliability, and versatility of other parameters. Further investigation revealed that if imaging with a different MT effect is added, free water is also affected through the MT effect, and as a result, it is possible to collect more detailed information on the entire biological tissue, and an analysis that takes the MT effect into account allows for a more accurate analysis of the entire tissue, including other parameters. Therefore, in the present embodiment indicated below, a four-pool model that takes the MT effect into account will be used as an example.

In the following, a medical data processing apparatus, a medical data processing method, a medical data processing program, and a magnetic resonance imaging apparatus according to the present embodiment will be described with reference to the accompanying drawings. In the following embodiments, elements assigned with the same reference signs are assumed to perform the same operations, and redundant descriptions thereof will be omitted as appropriate.

First Embodiment

A medical data processing apparatus according to a first embodiment will be described with reference to the block diagram of FIG. 1.

A medical data processing apparatus 1 includes processing circuitry 2, an input interface 4, a communication interface 6, and a memory 8.

The processing circuitry 2 includes an acquisition function 21, a generation function 22, a reconstruction function 23, and an optimization function 24. The processing circuitry 2 includes a processor (not shown) as a hardware resource.

The acquisition function 21 acquires imaging data acquired by executing spoiled gradient echo imaging and coherent gradient echo imaging at different flip angles.

The generation function 22 generates a low-rank approximate image set, which is a set of low-rank approximated images, from the imaging data.

The reconstruction function 23 reconstructs one or more parameter maps using the low-rank approximate image set and a multi-pool model related to water exchange in a biological tissue, the multi-pool model including plural free waters and bound water that performs magnetization exchange with the free waters.

The optimization function 24 performs optimization processing related to data consistency.

A training function 25 trains first and second neural networks to be described later, to generate first and second trained models.

The input interface 4 includes a circuit that receives various instructions and information inputs from a user. The input interface 4 includes, for example, a circuit related to a pointing device such as a mouse or an input device such as a keyboard. The circuit included in the input interface 4 is not limited to the circuit related to a physical operational component, such as a mouse or a keyboard. For example, the input interface 4 may include an electrical signal processing circuit that receives an electrical signal corresponding to an input operation from an external input device provided separately from the medical data processing apparatus 1 and outputs the received electrical signal to various circuits.

The communication interface 6 executes data exchange with an external device by a wired or wireless connection.

The memory 8 stores imaging data, a low-rank approximate image set, a weight coefficient related to a neural network, a trained model, a parameter map, etc., used or generated by the medical data processing apparatus 1. The memory 8 is a semiconductor memory element, such as a random access memory (RAM) and a flash memory, a hard disk drive (HDD), a solid state drive (SSD), an optical disk, etc. The memory 8 may be a CD-ROM drive, a DVD drive, or a drive which reads and writes various types of information from and to a portable storage medium such as a flash memory.

The various functions in the processing circuitry 2 are stored in the memory 8 in a form of a program executable by a computer. The processing circuitry 2 is a processor for reading out the programs corresponding to these various functions from the memory 8 and executing them to realize the functions corresponding to the programs. In other words, the processing circuitry 2 that has read the programs has the plurality of functions, etc. shown in the processing circuitry 2 of FIG. 1.

FIG. 1 illustrates the case where the various functions are realized in single processing circuitry 2; however, the processing circuitry 2 may be constituted by a combination of a plurality of independent processors, and the functions may be realized by the processors respectively executing the programs. In other words, each of the above-described functions may be formed as a program, and a single piece of processing circuitry may execute each program, or a specific function may be implemented in exclusive, independent program-execution circuitry.

Next, a concept of the multi-pool model assumed in the first embodiment, which is characterized by the inclusion of plural free waters and bound water that performs magnetization exchange therewith, will be described with reference to FIG. 2. The bound water here is water that is bound to biomolecules such as proteins and lipids, has a very fast T2 relaxation time of several tens of μs or less, and causes the MT effect by performing magnetization exchange with the free water. The bound water according to the present embodiment contains protons that cause the MT effect, such as protons of macromolecules (proteins, lipids, etc.), which cause the MT effect.

Figure 2:
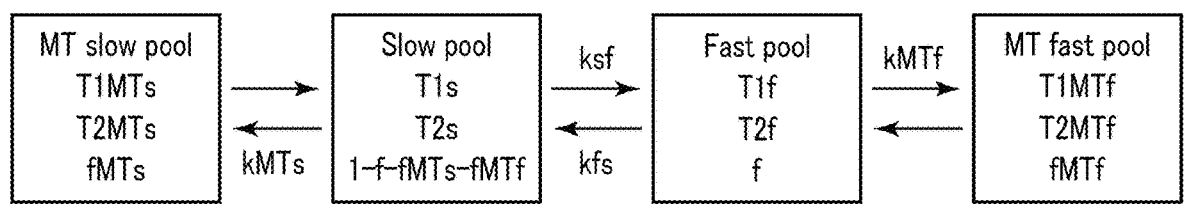
FIG. 2 is a conceptual diagram of a multi-pool model assumed in the first embodiment.

FIG. 2 is a conceptual diagram of a multi-pool model, i.e., a four-pool model here, that includes bound water in addition to free water that can move relatively freely in a biological tissue, and free water that is restricted in movement. Hereinafter, the four-pool model is assumed as a multi-pool model characterized by the inclusion of plural free waters and bound water that performs magnetization exchange therewith. Specifically, two types of free water and two types of bound water that performs magnetization exchange therewith are assumed. For the sake of explanation, the two types of free water are referred to as a slow pool and a fast pool, bound water that performs magnetization exchange with the slow pool is referred to as an MT-slow pool, and bound water that performs magnetization exchange with the fast pool is referred to as an MT-fast pool.

The MT-slow pool is assumed to perform magnetization exchange with the slow pool. The slow pool is assumed to perform magnetization exchange with the MT-slow pool and the fast pool. The fast pool is assumed to perform magnetization exchange with the slow pool and the MT-fast pool. The MT-fast pool is assumed to perform magnetization exchange with the fast pool. According to that four-pool model, the MT effect is taken into account and parameters such as an existence amount of the MT pools (MT-slow and MT-fast pools) and an exchange rate related to the bound water are set.

Here, relaxation times T1 and T2 of the slow pool are defined as "T1s" and "T2s". Relaxation times T1 and T2 of the fast pool are defined as "T1f" and "T2f". Relaxation times T1 and T2 of the MT-slow pool are defined as "T1MTs" and "T2MTs". Relaxation times T1 and T2 of the MT-fast pool are defined as "T1MTf" and "T2MTf".

A proton ratio of the MT-slow pool is defined as "fMTs" and a proton ratio of the MT-fast pool is defined as "fMTf" if the total is set to 1. Therefore, a proton ratio of the slow pool can be expressed as "1−f−fMTs−fMTf".

Furthermore, an exchange rate from the slow pool to the fast pool is defined as "ksf". An exchange rate from the fast pool to the slow pool is defined as "kfs". An exchange rate from the slow pool to the MT-slow pool is defined as "kMTs", and an exchange rate from the fast pool to the MT-fast pool is defined as "kMTf". An exchange rate from the MT-slow pool to the slow pool and an exchange rate from the MT-fast pool to the fast pool can be expressed as "kMTs×(1−f−fMTs−fMTf)/fMTs" and "kMTf·f/fMTf", respectively, from detail balancing.

Thus, the four-pool model has 14 independent parameters, but it is generally known that they can be approximated as "T1MTs=T1s" and "T1MTf=T1f". In the case of the brain, the MT pools are water molecules strongly bound to macromolecules, respectively, and their motion is strongly restricted, so their T2 values, i.e., values of T2MTs and T2MTf, can be excluded from the independent parameters by setting them as fixed values. In that case, the total number of parameters can be reduced by 4, so the number of independent parameters is 10.

The number of independent parameters of the four-pool model is not limited to 10, and the number of independent parameters may be 8 in the same manner as the two-pool model assuming a slow pool and a fast pool. Note that even though the number of independent parameters is eight, the conditions considered are different from the eight parameters in the two-pool model because the MT-slow and MT-fast pools for the bound water are considered as fixed values. Of course, conditions can be set such that T2MTs is a fixed value and T2MTf is considered as an independent parameter, and the independent parameter can be set discretionarily.

In the present embodiment, the plural free waters is not limited to two types of free water: free water that is relatively free to move and free water that is restricted in movement, but may include other types of free water. For example, in the head, free water can be broadly classified into three types: extracellular fluid, intracellular fluid, and myelin water, and these three can be included as plural free waters.

In the present embodiment, the four-pool model is assumed as the multi-pool model, but the configuration is not limited thereto; the number of pools can be increased or decreased depending on how many types of tissues with significantly different shapes exist in the biological tissue.

Next, an operation of the medical data processing apparatus according to the first embodiment will be described with reference to the flowchart of FIG. 3.

In step S301, the processing circuitry 2, with the acquisition function 21, acquires imaging data. The imaging data is collected by executing multiple spoiled gradient echo imagings and coherent gradient echo imagings in succession, while changing the flip angle.

The imaging data is considered here as N pieces of imaging data generated by sparse sampling of a subject for each RF shot. N is an integer of 2 or more. The sparse sampling, in the present embodiment, indicates sampling that is at a thinner interval than a sampling interval that should normally be performed, or sampling that has a lower number of samples than the number of samples that should normally be obtained.

In step S302, the processing circuitry 2, with the generation function 22, generates a sparse-sampling low-rank approximate image set from the imaging data. Using preset M sets of N weight coefficients, the generation function 22 generates M sparse-sampling low-rank image sets by multiplying N pieces of first data by corresponding weight coefficients for each of the sets and adding them so as to low-rank approximate the N pieces of first data. M is an integer less than N.

In step S303, the processing circuitry 2, with the generation function 22, estimates a full-sampling low-rank approximate image from the sparse-sampling low-rank approximate image by using a first trained model. The first trained model is a model in which the first neural network is trained to output M full-sampling low-rank approximate image sets obtained by inputting M sparse-sampling low-rank approximate image sets and low-rank approximating, in the same manner as in the imaging data, N full-sampling data generated by full-sampling the subject. In a case where the full sampling and the sparse sampling are not distinguished, they are referred to simply as a low-rank approximate image set. The full sampling indicates sampling at a sampling interval that should normally be performed, or sampling having the number of samples that should normally be obtained.

In step S304, the processing circuitry 2, with the optimization function 24, performs optimization processing for data consistency on the full-sampling low-rank approximate image. The data consistency indicates consistency between k-space data acquired by imaging an estimated full-sampling low-rank approximate image and actually measured k-space data. Specifically, the optimization processing may be performed by alternately repeating estimation of a full-sampling low-rank approximate image using the first trained model and estimation of a full-sampling low-rank approximate image from imaging data by a back projection method with a conjugate gradient (CG) method.

More specifically, the obtained full-sampling low-rank approximate image may be inverse transformed to generate k-space data for checking, which is sparse-sampled k-space data for consistency checking, and then whether a value of an error function, which includes an evaluation of a difference between that k-space data for checking and the k-space data of the imaging data acquired in step S301, is a threshold value or less may be determined. If the value of the error function is the threshold value or less, a convergence condition is satisfied, and the process proceeds to step S305. If the value of the error function is greater than the threshold value, the full-sampling low-rank approximate image may be corrected and the same process may be repeated until the convergence condition is satisfied.

For example, the estimation of the full-sampling low-rank approximate image set by the above convolutional neural network and the estimation of the full-sampling low-rank approximate image set from the imaging data by the back projection method using the CG method can be repeated using an ADMM (alternating direction method of multipliers) to achieve convergence.

This method also optimizes data consistency, allowing for more reliable estimation of a full-sampling low-rank approximate image. For a detailed method using the ADMM or an approximate ADMM similar to the ADMM, which is executed by the optimization function 24, the method described in Japanese Patent Application KOKAI Publication No. 2021-10408, for example, may be used.

In step S305, the processing circuitry 2, with the generation function 22, sets a pixel value (voxel value) of a full-sampling low-rank approximate image set as a low-rank approximate value set, and estimates a parameter value using a second trained model based on the low-rank approximate value set. Details of the second trained model will be described later with reference to FIGS. 12, 13, etc.

In step S306, the processing circuitry 2, with the reconstruction function 23, for example, determines whether or not the process in step S305 has been completed for all the voxels. If the process has been completed for all the voxels, the process proceeds to step S307, and if there is an unprocessed voxel, the process returns to step S305 and the same process is repeated.

In step S307, the processing circuitry 2, with the reconstruction function 23, generates a parameter map by which the parameter estimation is executed for all the voxels.

In step S303, for M (rank M) sparse-sampling low-rank approximate image sets as inputs, the number of full-sampling low-rank approximate image sets as output is also desirably M (rank M), but the output accuracy can be improved by increasing the rank number of inputs relative to the rank number of outputs. In addition, by reducing the rank number of inputs relative to the rank number of outputs, the output accuracy is slightly reduced, but the speed can be increased in terms of the amount of memory and calculation speed. Thus, the rank number of inputs and the rank number of outputs can be adjusted as appropriate according to the purpose of use. That is, it is not limited to those that output all the M sets. In the following example, a case in which the rank number of inputs and the rank number of outputs are the same will be described.

The optimization processing in step S304 is not required, and step S305 may be performed after step S303.

Next, an example of an imaging sequence according to the first embodiment will be described with reference to FIG. 4.

Figure 4:
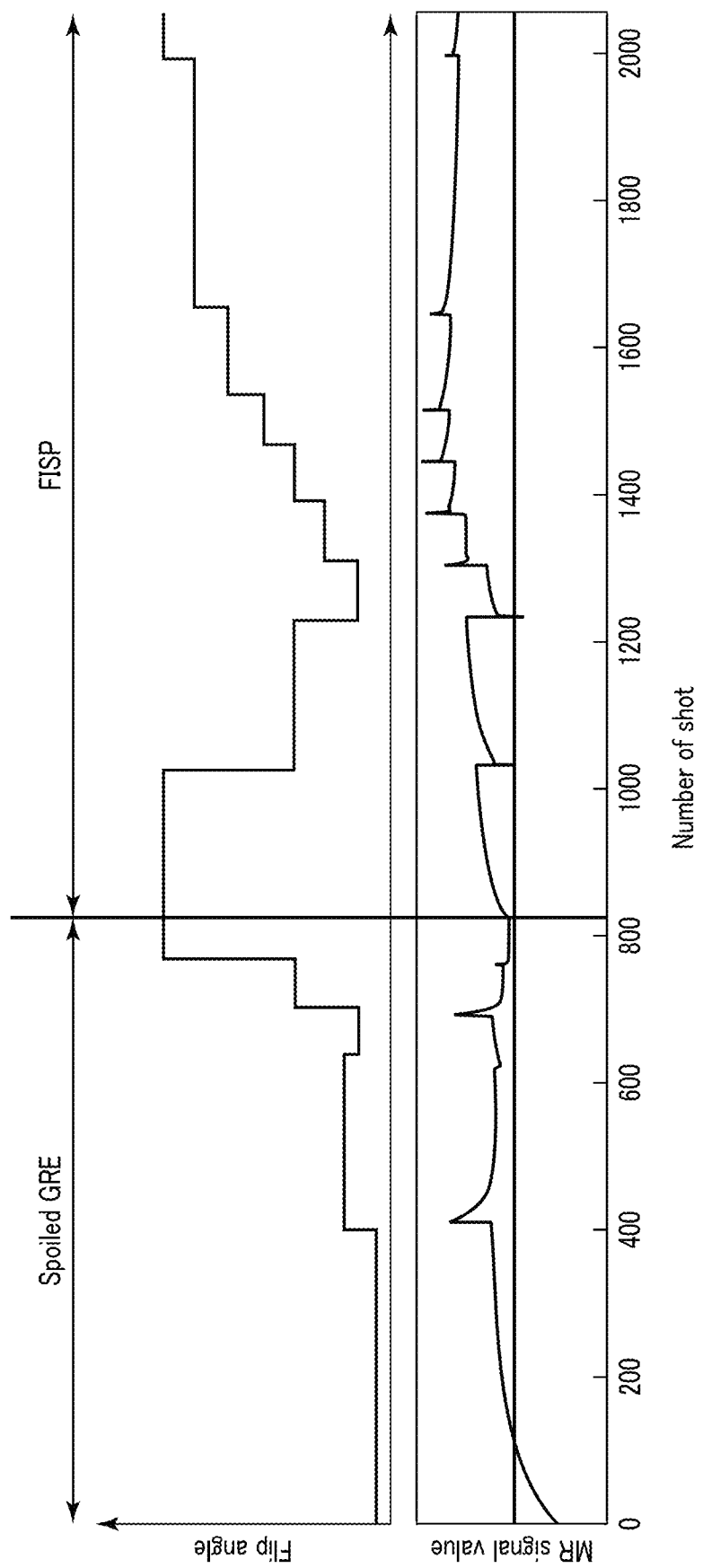
FIG. 4 is a diagram showing an example of an imaging sequence according to the first embodiment.

An upper part of FIG. 4 shows a time series variation with the number of shots relative to flip angles. A lower part of FIG. 4 shows a time series variation with the number of shots relative to MR signal values.

Here, spoiled gradient echo (hereafter referred to as spoiled GRE) and coherent gradient echo (hereafter referred to as coherent GRE) are performed as the imaging sequence.

In the spoiled GRE, transverse magnetization is spoiled for each RF excitation (in each shot), but RF spoiling may be combined. The RF spoiling is a technique to spoil transverse magnetization by modulating an RF phase.

In the spoiled GRE imaging, transverse magnetization is spoiled in each shot, so the MR signal includes little information on transverse magnetization relaxation, but mainly information on longitudinal magnetization relaxation and B1 distribution. On the other hand, in the coherent GRE imaging, information on all longitudinal and transverse magnetization relaxation, $B_1$ distribution, and possibly $B_0$ distribution are included. By combining the two, the longitudinal magnetization relaxation, transverse magnetization relaxation, $B_1$ distribution, and possibly $B_0$ distribution can be accurately separated.

As an example of coherent GRE, fast imaging with FISP is assumed.

The coherent GRE is not limited to the FISP, but can also be used with imaging sequences that perform full rewinding, such as bSSFP, but in this case, the $B_0$ distribution itself will also need to be mapped because of an influence of the static magnetic field distribution ($B_0$ distribution). To remove the influence of the $B_0$ distribution, a method in which a gradient spoiling is applied in one direction, such as the FISP, may be used. For this reason, a case of using the FISP as coherent GRE imaging will be described below.

In the imaging sequence shown in FIG. 4, the first half is imaged with the spoiled GRE and the second half is imaged with the FISP, but an IR pulse (adiabatic 180° pulse) is applied at the very beginning to invert longitudinal magnetization by 180°. At the end of the spoiled GRE, short-time imaging is executed at a large flip angle to saturate the longitudinal magnetization and bring it close to zero. This allows oscillation of magnetization to be suppressed at the start of FISP imaging, thus increasing the accuracy of the analysis. TR/TE can be fixed throughout the sequence. As an example, it may be set such that TR=7.0 ms and TE=3.5 ms. Note that TR/TE may be changed for each imaging.

As a comparison, in the case of spoiled GRE imaging alone, no information on transverse magnetization relaxation is available and thus the analysis cannot be performed. In the case of coherent GRE imaging alone, it is difficult to separate the information, making the analysis difficult.

Information on the MT effect can be obtained from the on-resonance MT effect due to RF pulses. That is, the flip angle is changed between the spoiled GRE and the coherent GRE, but the $B_1$ intensity must be changed to change the flip angle, which naturally results in imaging with a different intensity of the on-resonance MT effect. In order to obtain more detailed information on the MT effect, a combination of imaging that actively changes the MT effect may be executed. In both cases, changes can also be made to the magnetization state of the free water undergoing magnetization exchange via the MT effect, allowing for more accurate parameter estimation of the overall multicompartment microstructure model. Thus, it is possible to achieve accuracy that cannot be obtained in the case of not taking the MT effect into account. Furthermore, if the MT effect is changed more aggressively, the amount of data obtained will increase, and thus higher accuracy can be obtained.

Next, another example of the imaging sequence according to the first embodiment will be described with reference to FIG. 5.

An upper part of FIG. 5 shows a time series variation with the number of shots relative to flip angles. A middle part of FIG. 5 shows a time series variation with the number of shots relative to RF pulse widths. A lower part of FIG. 5 shows a time series variation with the number of shots relative to MR signal values. The imaging sequence is the same as in FIG. 4.

To execute imaging that changes an influence of the MT effect, the RF pulse width may be changed to execute imaging. The flip angle is proportional to an integrated value of an RF field strength, while the on-resonance MT effect is proportional to an integrated value of RF power. On the other hand, since the RF power is proportional to a square of the RF field strength, halving the RF pulse width doubles the MT effect, even though the flip angle is the same. Thus, even in the imaging at the same flip angle, a different MT effect can be obtained by executing imaging with a different RF pulse width. This allows information on the MT effect to be extracted with even greater sensitivity. In order to obtain more detailed MT information, an off-resonance MT pulse may be inserted before the on-resonance RF pulse for excitation. Furthermore, by combining imaging with a different off-resonance frequency of the added off-resonance MT pulse, even more detailed information on the MT effect can be obtained. For this reason, it is desirable to use the off-resonance MT pulse especially when T1 and T2 of the MT pool, that is, bound water, must also be determined independently as parameter maps.

Next, an example of radial scanning assumed in the present embodiment will be described with reference to FIG. 6.

Figure 6:
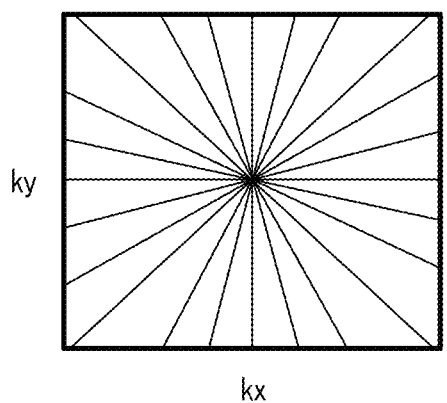
FIG. 6 is a diagram showing one example of radial scanning assumed in the present embodiment.

FIG. 6 shows a trajectory of the radial scanning in k-space where the horizontal axis is kx and the vertical axis is ky. It is assumed that an angle of spokes of the radial scanning is increased (rotated) by a golden angle ($2\pi/(1+\sqrt{5})$) for each shot. However, this is only one example, and a swing of the spoke angle is not limited to the golden angle. The spoke angle may be changed by other methods.

As a k-space trajectory, the spoke desirably passes through the k-space center for each shot. This is because the quality of a signal for each shot is desirably as uniform as possible in order to obtain a low-rank approximate image set from acquired imaging data. Therefore, radial, spiral, variable-density spiral (VDS) trajectories, etc. are desirably used, but other scanning methods are also acceptable, including but not limited to them. A scan method and a k-space trajectory in which the spoke does not pass through the center of k-space for each shot may be used.

Next, a concept and an example of generating a sparse sampling low-rank approximate image will be described with reference to FIG. 7. Here, an image is assumed as data.

In each shot (1, 2, 3, 4, . . . ), MR signals are collected along a trajectory for one spoke in the radial scanning and k-space is filled to acquire k-space data. Specifically, in the first shot, MR signals are collected along a right-down spoke, and in the second shot, MR signals are collected along a right-up spoke. Thus, sparse sampled sparse-sampling k-space data 701 is acquired for each shot.

For the sparse-sampling k-space data 701 for each shot, the k-space data is multiplied by a weight coefficient 702, $W_{ij}$, and added together to generate i pieces of k-space data 703. i and j are integers of 1 or more. The weight coefficient 702, $W_{ij}$, may be prepared in a plural number corresponding to the rank number, and represents a weight coefficient to multiply k-space data of the jth shot when creating a low-rank approximate image of rank i.

By executing an inverse Fourier transform, such as IFFT (Inverse fast Fourier Transform), on each of the i pieces of k-space data 703, i sparse-sampling low-rank approximate images 704 are generated.

To obtain the weight coefficient 702, a set of transient signals acquired when imaging with the sequence described above for various parameter values is first created by simulation based on the four-pool model. By a principal component analysis of the set of transient signals created, a necessary rank weight coefficient can be calculated. In the rank, the numbers 1, 2, 3, . . . are assigned in the order from the largest to smallest singular values of the principal component analysis (PCA). In addition to the principal component analysis, a multivariate analysis such as singular value decomposition (SVD) and a dimensionality compression process such as nonnegative matrix factorization (NMF) may be applied. As a result, i sets of weight coefficients for executing low-rank approximation can be obtained.

Figure 7:
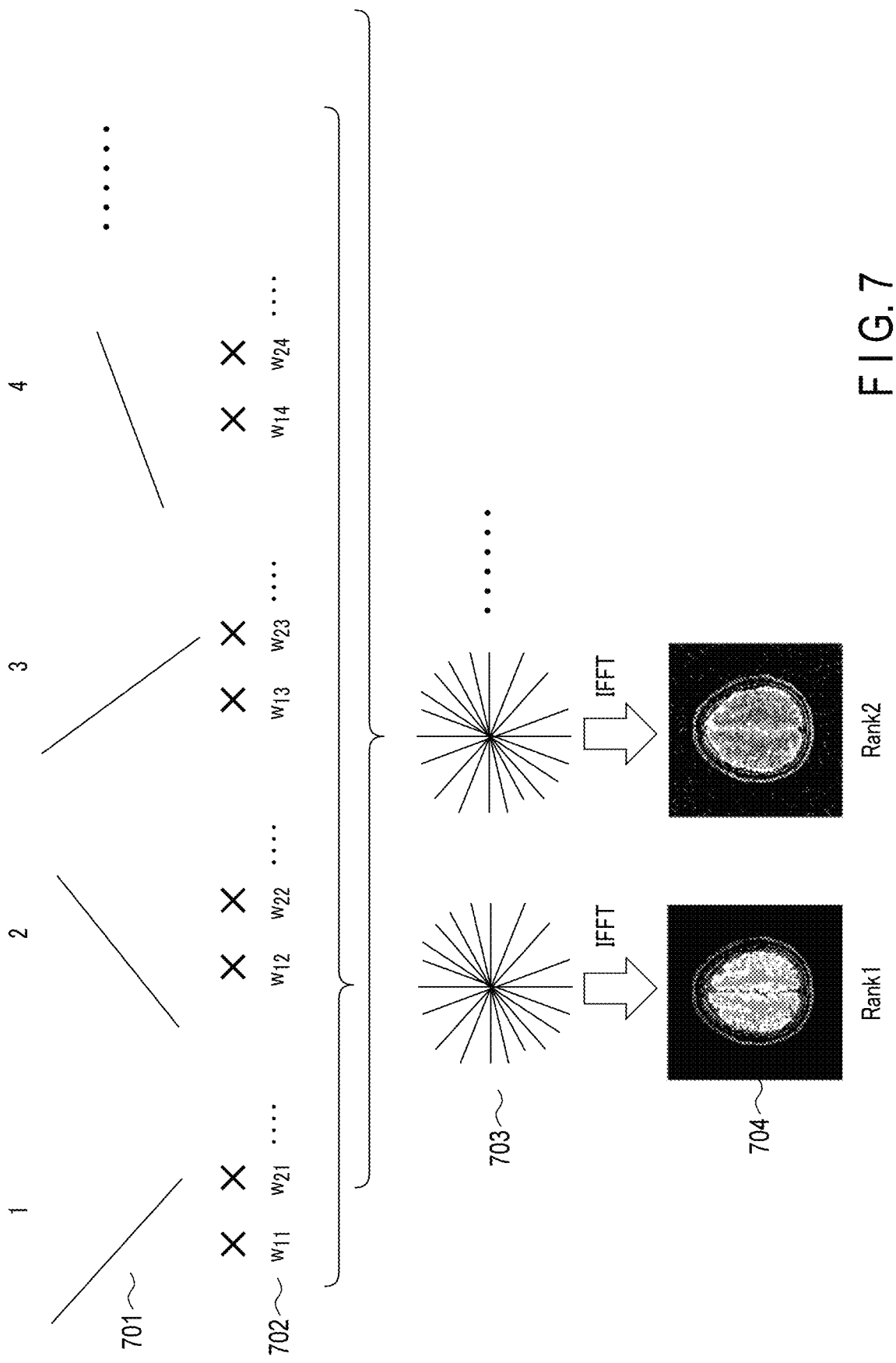
FIG. 7 is a diagram showing a concept and an example of generating a sparse-sampling low-rank approximate image.

The example of radial scanning is shown in FIG. 7, but even for trajectories using other scan methods, i pieces of k-space data can be obtained by multiplying all k-space data acquired for each shot by weight coefficients and adding them together by the same method.

However, the low-rank approximate image created by the above method is a sparse-sampling low-rank approximate image because basically there is only one trajectory signal (spoke) for each shot. Thus, the image may contain so many artifacts that attempting to obtain a parameter map directly from the sparse-sampling low-rank approximate image may not provide a necessary accuracy. Therefore, a full-sampling low-rank approximate image is desirably used to obtain the parameter map.

Next, a concept and an example of generating a full-sampling low-rank approximate image will be described with reference to FIG. 8.

Figure 8:
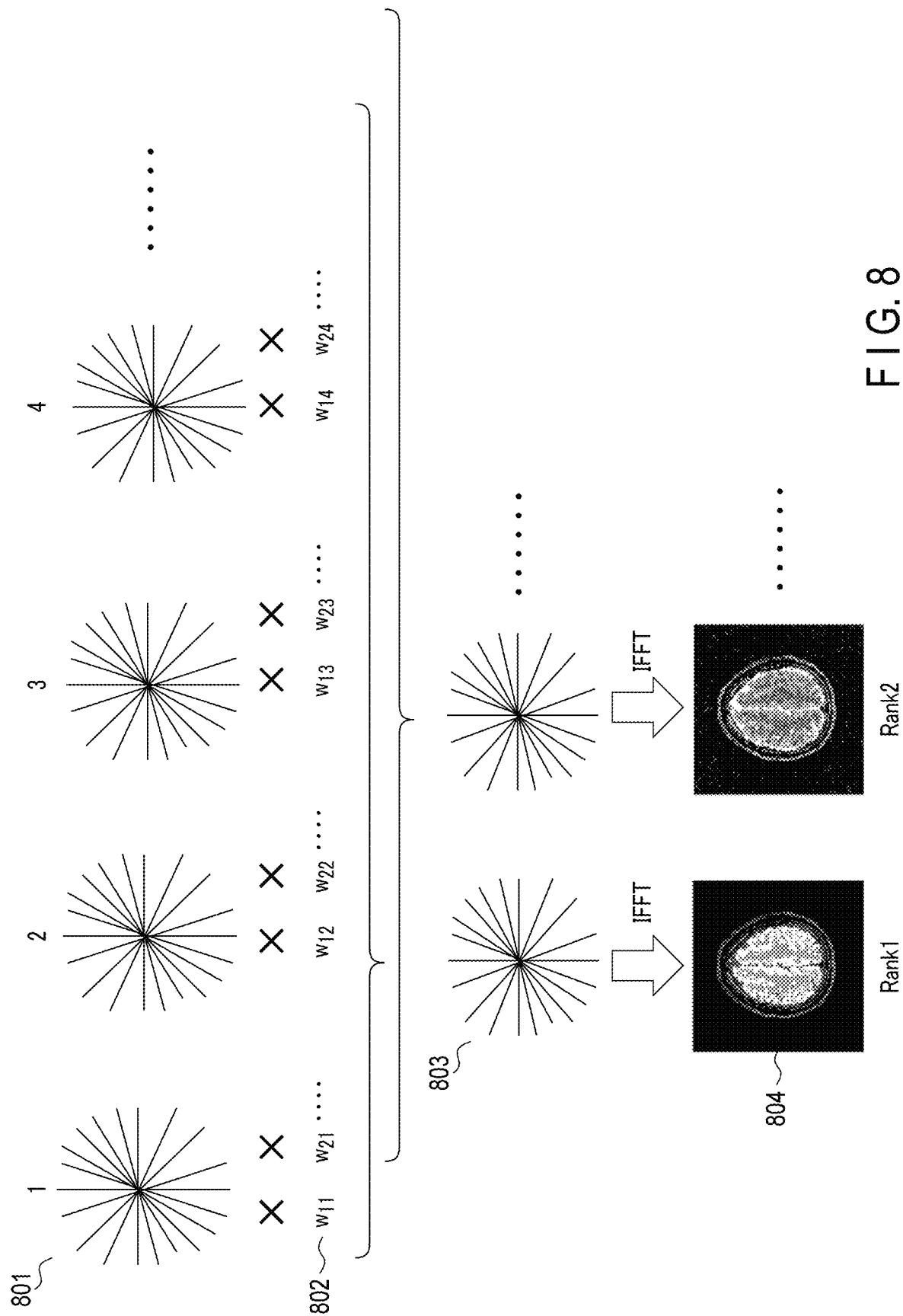
FIG. 8 is a concept and an example of generating a full-sampling low-rank approximate image.

FIG. 8 shows a concept diagram of a method of creating a full-sampling low-rank approximate image. In radial imaging, for example, if an image of each shot (1, 2, 3, 4, . . . ) can be fully sampled in 400 spokes, imaging based on the above sequence is executed 400 times, while changing the angle of an initial spoke. Combining them and collecting 400 trajectory signals (spokes) for each shot, full-sampling k-space data 801 for each shot can be acquired.

By multiplying the full sampling k-space data 801 for each shot by a weight coefficient 802, $W_{ij}$, and adding them together, i pieces of k-space data 803 are generated. The weight coefficient 802 is identical to the weight coefficient 702 in FIG. 6. An inverse Fourier transform, such as IFFT, is executed on each of the i pieces of k-space data 803 to generate i full-sampling low-rank approximate images 804.

However, the imaging time for this case is 400 times longer than the sparse sampling case in FIG. 7. Thus, in the present embodiment, a full-sampling low-rank approximate image is estimated from a sparse-sampling low-rank approximate image by using a trained model such as a neural network.

Next, the first neural network at the time of training will be described with reference to FIG. 9.

A convolutional neural network is assumed as the first neural network. At the time of training of the convolutional neural network, for example, a simulation is performed in which a number of numerical phantoms composed of a four-pool model are imaged by the sequence described above. Through that simulation, a number of pairs of a full-sampling low-rank approximate image set and a sparse-sampling low-rank approximate image set, having the same rank number, are prepared as training data. The sparse-sampling low-rank approximate image set can be generated by simulation assuming that one spoke is imaged in one shot.

The processing circuitry 2, with the training function 25, trains the convolutional neural network with the sparse-sampling low-rank approximate image set as input data and the full-sampling low-rank approximate image set as ground truth data among the training data. In the present embodiment, the imaging data is divided into a plurality of regions, and a low-rank approximate image set is generated in each region. Specifically, an example is shown in which spoiled GRE imaging data and FISP imaging data are individually subjected to principal component analyses, each using weight coefficients from ranks 1 to 13, creating a total of 26 low-rank approximate image sets, but the data may be subjected to a principal component analysis in a lump.

Figure 9:
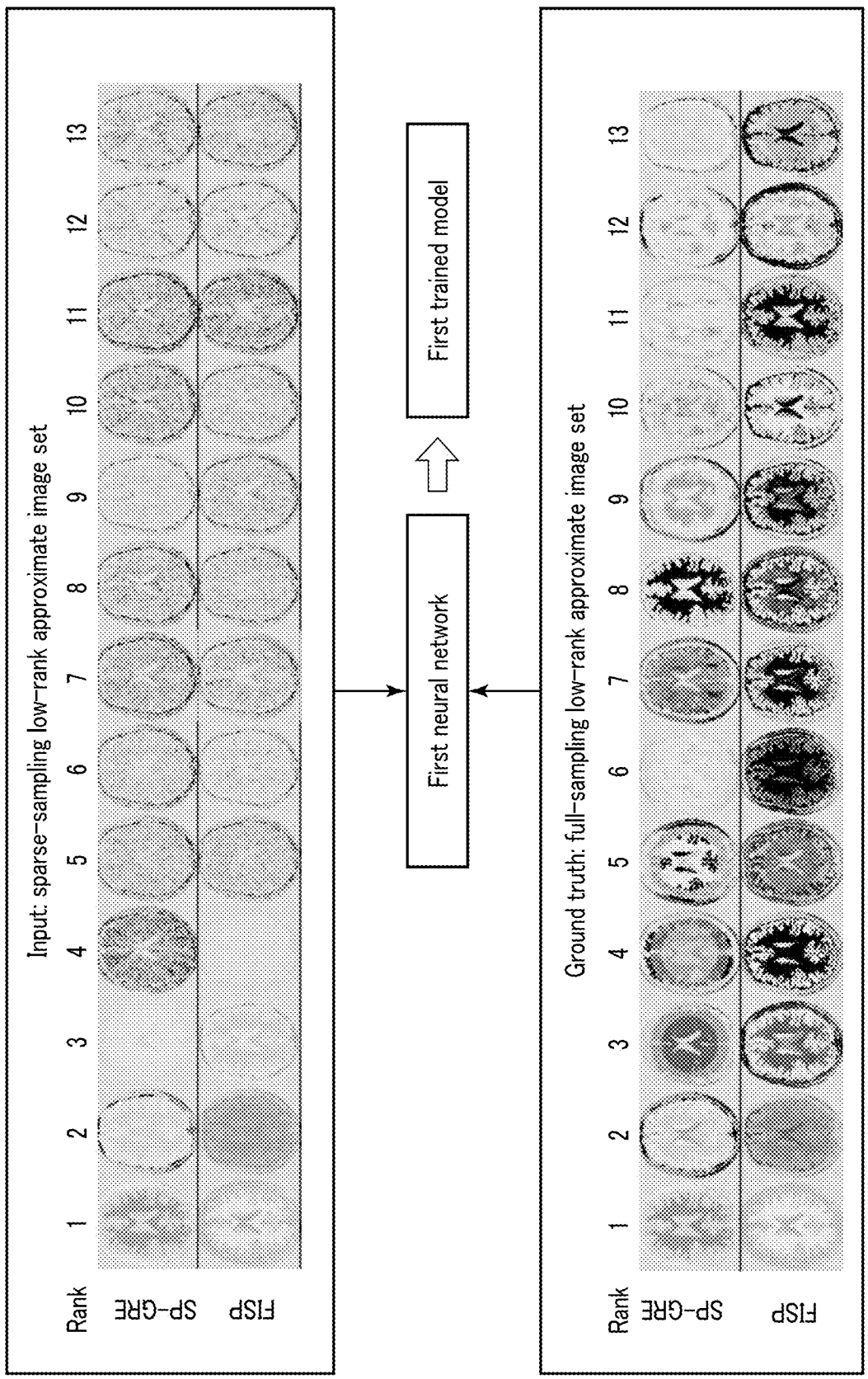
FIG. 9 is a diagram showing an example of a first neural network at the time of training.

In the example in FIG. 9, input data is a set of 13 sparse-sampling low-rank approximate images acquired by the spoiled GRE imaging and 13 sparse-sampling low-rank approximate images acquired by the FISP imaging. A set of 13 full-sampling low-rank approximate images by the spoiled GRE imaging and 13 full-sampling low-rank approximate images by the FISP imaging is ground truth data. In the example of FIG. 9, since pixel values decrease rapidly as the rank number increases, normalized data is used so that dispersion of the pixel values is 1 at each rank. In the sparse-sampling low-rank approximate image set, the data is normalized in a state of including spatial noise, so the data is appropriately magnified and displayed. It is desirable to perform normalization as appropriate during training.

In training, for example, parameters of the convolutional neural network may be updated and the network optimized so that a loss function, designed by a mean square error between the ground truth data and the first neural network or cross-entropy, is minimized. Since a general training method for machine learning may be used for training the neural network, a detailed description thereof is omitted here. Upon completion of training, a first trained model of the first neural network is generated.

Examples of convolutional neural networks include U-Net and DenseNet, but any neural network structure used in the machine learning field may be used.

Next, the first neural network at the time of inference will be described with reference to FIG. 10.

At the time of inference, as shown in FIG. 10, a sparse-sampling low-rank approximate image set is input to a trained model and a full-sampling low-rank approximate image set is output from the trained model. Each image in the sparse-sampling low-rank approximate image set is noisy, but by using the trained model, the full-sampling low-rank approximate image set with reduced noise can be obtained.

Next, a process of generating a parameter map from a full-sampling low-rank approximate image set will be described with reference to FIGS. 11 to 13.

With the reconstruction function 23, a parameter value is generated by applying a second trained model to each pixel value, or each voxel, of the full-sampling low-rank approximate image. A parameter map can be generated based on the parameter values of all the voxels.

First, a training process of a second neural network to obtain the second trained model will be described.

Figure 11:
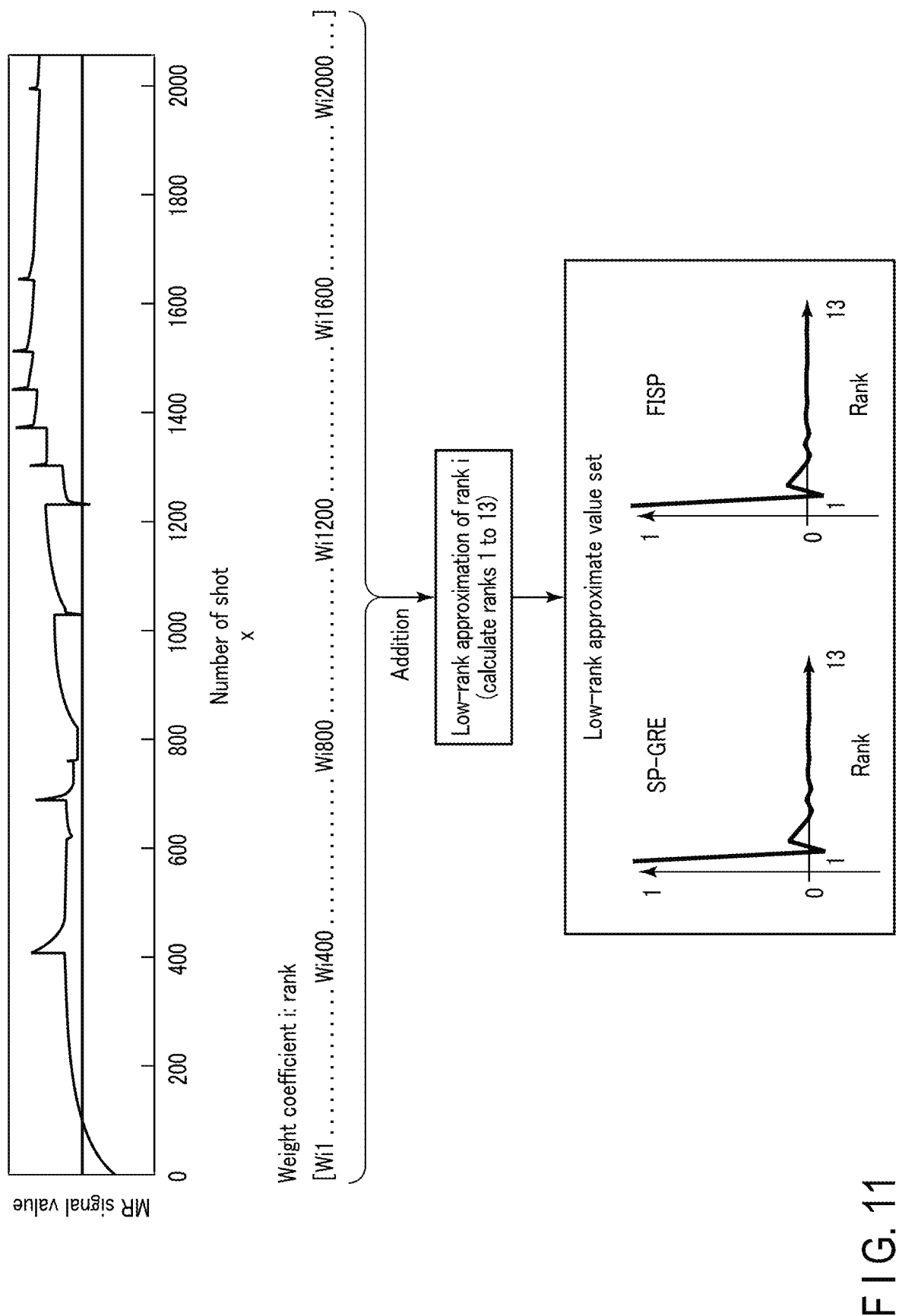
FIG. 11 is a conceptual diagram of generating a low-rank approximate value set from a transient signal.

FIG. 11 is a conceptual diagram of generating a low-rank approximate value set from a transient signal.

In FIG. 11, a single voxel simulation with the imaging sequence shown in FIG. 4 or 5 is executed using a four-pool model. Transient signals for a number of parameter value sets obtained through the simulation are generated.

From the transient signals obtained through the simulation, by using $W_{ij}$, the weight coefficient 802 used to create the full-sampling low-rank approximate image set, a low-rank approximate value of a required rank number is determined by multiplying an MR signal value of each shot by the weight coefficient $W_{ij}$ and adding them together. Here, the low-rank approximation is executed by multiplying a corresponding shot j by $W_{ij}$ (j=1, 2, . . . ) as the weight coefficient of rank i and adding them together to obtain a low-rank approximate value. That is, a set of 13 (ranks 1 to 13) full-sampling low-rank approximate image voxel values matches a set of 13 (ranks 1 to 13) low-rank approximate values. FIG. 11 shows a graph of a low-rank approximate value set as an example. In the graph, the vertical axis indicates the value of the low-rank approximate value, and the horizontal axis indicates the rank number. A graph of a low-rank approximate value set of ranks 1 to 13 related to the spoiled GRE (SP-GRE) and a graph of a low-rank approximate value set of ranks 1 to 13 related to the FISP are shown. They are simply referred to as the low-rank approximate value set.

A number of low-rank approximate value sets and parameter value sets generated in this manner are prepared.

Next, the second neural network at the time of training is shown in FIG. 12.

The processing circuitry 2, with the training function 25, trains the second neural network with a low-rank approximate value set as input data and a parameter value set as ground truth data. Input and output are desirably normalized as appropriate for training.

The second neural network is assumed to be, for example, a tightly coupled neural network, but is not limited thereto and any network in the machine learning field may be used. In addition, a general training method for machine learning may be used for training a convolutional neural network. Upon completion of training, the second trained model of the second neural network is generated.

Next, the second neural network at the time of inference is shown in FIG. 13.

At the time of inference, as shown in FIG. 13, a pixel value set (i.e., a low-rank approximate value set) of a full-sampling low-rank approximate image based on imaging data is input to the second trained model, and an estimated parameter value set is output. This allows for a one-to-one mapping of parameter values in the four-pool model and parameter values can be estimated.

In the present embodiment, the first and second neural networks are trained to generate the first and second trained models, respectively, but the first and second trained models may be connected and fine-tuned end-to-end. Thus, adaptation processing, commonly performed to improve accuracy in the machine learning field, may further be performed.

Figure 14:
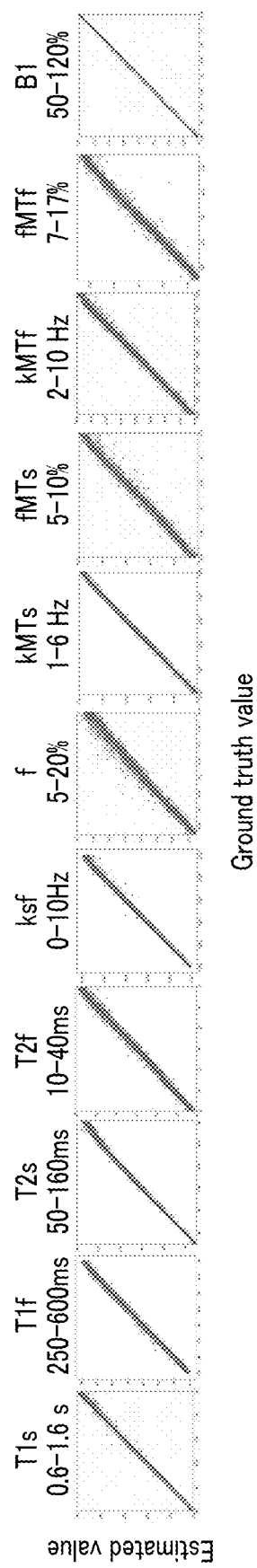
FIG. 14 is a diagram showing an example of a calibration curve for an estimated value of each parameter value.

Next, an example of a calibration curve for an estimated value of each parameter value is shown in FIG. 14.

FIG. 14 shows calibration curves for 11 parameter values (T1$s$, T1$f$, T2$s$, T2$f$, ksf, f, kMTs, fMTs, kMTf, fMTf, B$_1$), in which a B$_1$ value is added to the 10 parameters described above in the four-pool model shown in FIG. 2. Here, B$_1$ is RF magnetic field distribution. In a graph of each calibration curve, the vertical axis indicates the estimated value and the horizontal axis indicates a ground truth value. As shown in FIG. 14, overall favorable estimation is made.

Next, an example of a parameter map to be generated will be described with reference to FIG. 15.

Figure 15:
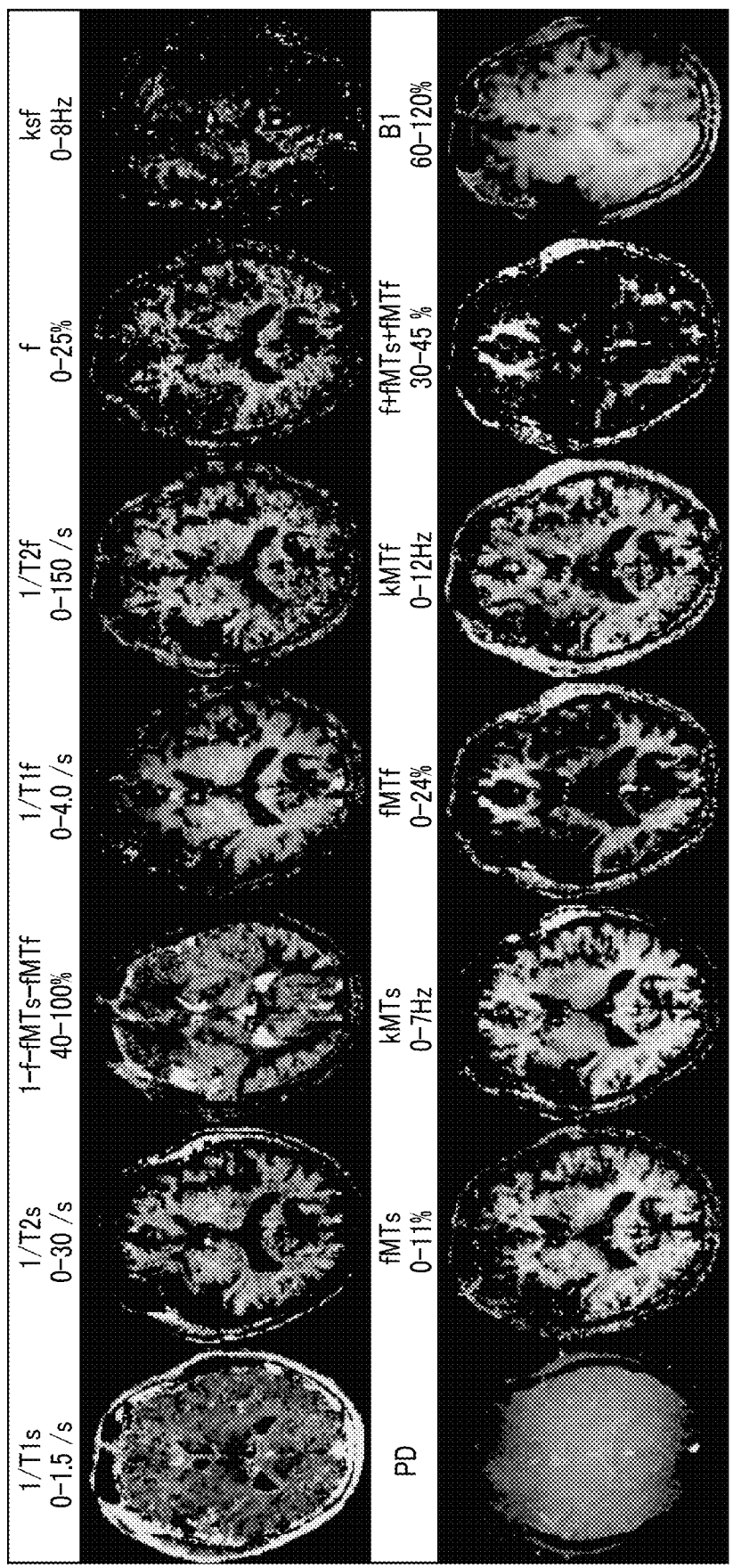
FIG. 15 is a diagram showing a parameter map generated from an estimated parameter value.

In addition to the parameter maps for the parameter values shown in FIG. 14, FIG. 15 shows a proton density map, a parameter map for a proton ratio (1−f−fMTs−fMTf) of a slow pool, and a parameter map for a proton ratio (f+fMTs+fMTf) of a non-slow pool.

A parameter value set is generated by inputting a pixel value set (i.e., a low-rank approximate value set) for each voxel of a full-sampling low-rank approximate image obtained by the imaging sequence shown in FIG. 4 into the second trained model. Parameter maps corresponding to 11 parameters are generated using the parameter value sets of all the voxels. Thereby, the parameter maps shown in FIG. 15 are generated. In the example in FIG. 15, a two-dimensional image of 256×256 pixels is taken in about 1 minute and analyzed in about 10 seconds, which can realize high-speed processing.

Although a two-dimensional image is described as an example, parameter maps can also be generated in the same way in three-dimensional imaging.

Other images can also be generated from a full-sampling low-rank approximate image. An example of generating other images based on a full-sampling low-rank approximate image is shown in FIG. 16.

FIG. 16 shows an example of generating a T1 map obtained by IR-GRE imaging and a T2 map obtained by CPMG (Carr Purcell Meiboom Gill) imaging.

In the IR-GRE, a longitudinal magnetization relaxation curve can be obtained for each voxel by executing imaging at different IR times many times, and by subjecting the curve to single exponential function fitting, a single-compartment T1 can be obtained. In the CPMG imaging, a transverse magnetization relaxation curve can be obtained for each voxel by executing imaging with different TEs many times, and by subjecting the curve to single exponential function fitting, a single-compartment T2 can be obtained.

These are apparent relaxation times, T1$a$ and T2$a$, obtained by single-compartment analysis. Currently, the single-compartment analysis is the mainstream method for quantifying T1 and T2 in MRI imaging, so it is sometimes desirable to determine T1$a$ and T2$a$ for comparison with the conventional techniques.

In this case, if the parameter map of the four-pool model is available, it is possible to obtain a relaxation curve for each voxel by performing simulation of executing imaging at different IR times in IR-GRE many times using the four-pool model and the parameter map, and to determine T1$a$ by subjecting the relaxation curve to single exponential function fitting. In the same way, a relaxation curve for each voxel can be obtained by performing simulation of executing imaging with different TEs in CPMG many times, and by subjecting the curve to single exponential function fitting, T2$a$ can be determined.

That is, once the parameter values of the four-pool model are determined, T1$a$ and T2$a$ determined in a particular sequence can be determined, such as T1 determined in the IR-GRE and T2 determined in the CPMG. On the other hand, as already described, the parameter values of the four-pool model can be determined for each pixel from the full-sampling low-rank approximate image.

Accordingly, the neural network can be trained so that a pixel value set (a low-rank approximate value set) of the full-sampling low-rank approximate image is used as an input and T1$a$ and T2$a$ as outputs.

In other words, a large number of data sets of low-rank approximate value sets and T1$a$ and T2$a$ may be created to let the second neural network learn correspondence relationships therebetween. This allows the second trained model to be used to create MP2REGE, a T1 map for imaging with IR-GRE, a T2 map for imaging with CPMG, etc. directly from the imaging data of the imaging sequence according to the first embodiment.

By doing the same, the medical data processing apparatus according to the first embodiment can also create various weighted images in a case of imaging with a specific imaging method and imaging parameters. The various weighted images are images used for image diagnosis, such as a T1 weighted image, a T2 weighted image, a T2* image, a FLAIR (fluid-attenuated inversion recovery) image, and a diffusion weighted image.

According to the first embodiment described above, multiple spoiled GRE imagings and coherent GRE imagings are continuously executed while changing the flip angle to obtain imaging data. A full-sampling low-rank approximate image is generated from a sparse-sampling low-rank approximate image using a first trained model. Parameter values are estimated from a low-rank approximate value set corresponding to a pixel value set for each voxel of the full-sampling low-rank approximate image using a second trained model. A parameter map is reconstructed by estimating parameter values for all voxels.

This allows for an accurate quantitative value map that takes into account the MT effect and B1 distribution, as well as a quantitative value map of the MT effect itself. Further, it can execute high-speed and reliable estimation with a practical resolution.

Modification of First Embodiment

In the first embodiment, a parameter map of a multi-pool model characterized by inclusion of plural free waters and bound water that performs magnetization exchange with the free waters is generated by obtaining a low-rank approximate image set based on the imaging sequence as shown in FIG. 4 or FIG. 5.

On the other hand, in the modification of the first embodiment, as an imaging sequence, spoiled GRE imaging and coherent GRE imaging are executed while continuously changing the flip angle for each shot. Thus, even if imaging is executed by changing the flip angle for each shot, a parameter map can be generated using a multi-pool model characterized by the inclusion of plural free waters and bound water that performs magnetization exchange therewith, as in the first embodiment.

Second Embodiment

Figure 17:
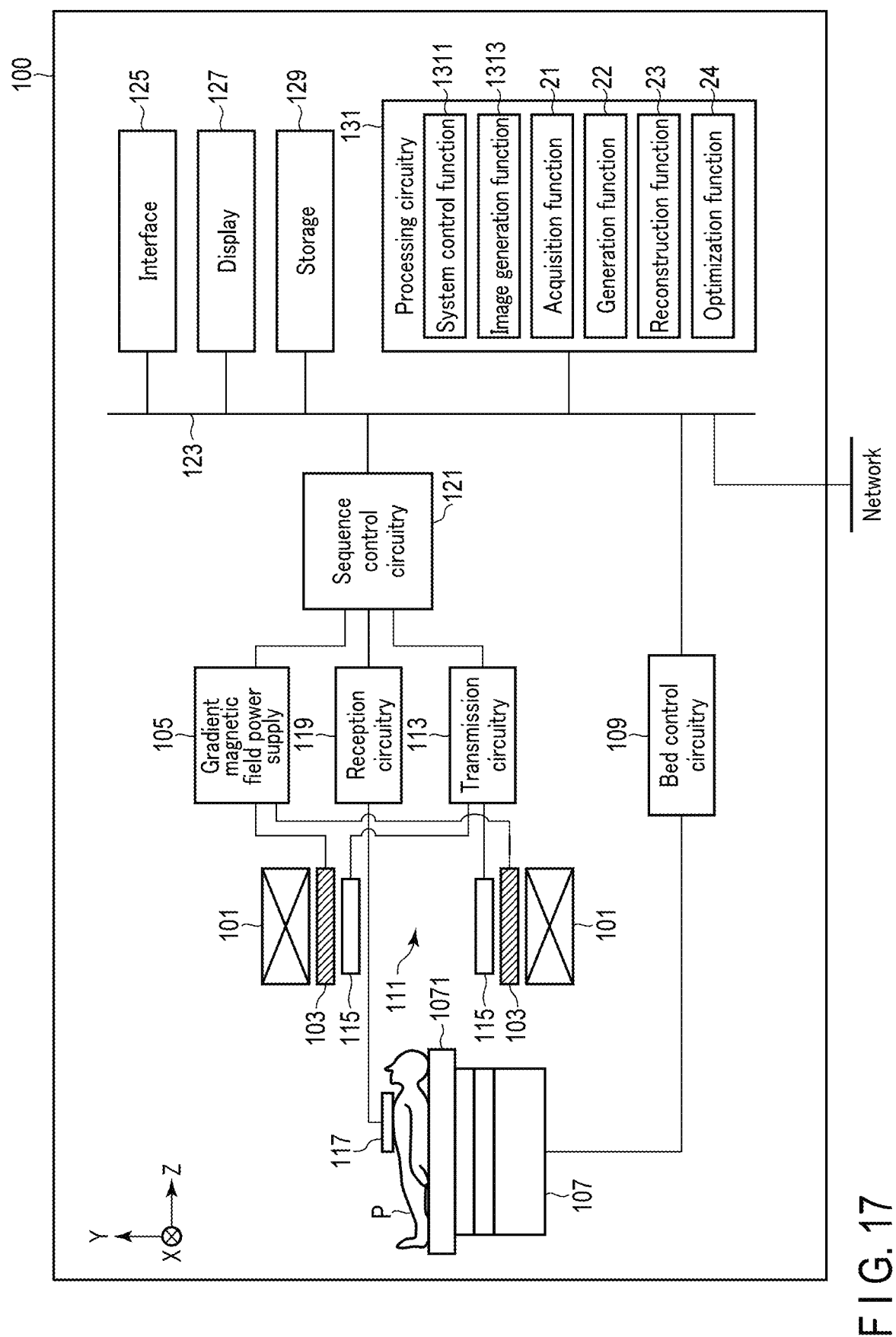
FIG. 17 is a diagram showing an overall configuration of a magnetic resonance imaging apparatus according to a second embodiment.

In a second embodiment, an overall configuration of a magnetic resonance imaging apparatus including the medical data processing apparatus according to the above-described embodiment will be described with reference to FIG. 17. FIG. 17 is a diagram showing a configuration of a magnetic resonance imaging apparatus 100 in the present embodiment.

As shown in FIG. 17, the magnetic resonance imaging apparatus 100 includes a static magnetic field magnet 101, a gradient magnetic field coil 103, a gradient magnetic field power supply 105, a bed 107, bed control circuitry 109, a transmitter coil 115, transmission circuitry 113, a receiver coil 117, reception circuitry 119, sequence control circuitry 121, a bus 123, an interface 125, a display 127, a storage 129, and processing circuitry 131. The magnetic resonance imaging apparatus 100 may have a hollow, cylindrical-shaped shim coil provided between the static magnetic field magnet 101 and the gradient magnetic field coil 103. A unit group that images a subject based on an imaging sequence and collects imaging data, represented by the transmission circuitry 113, the reception circuitry 119, and the sequence control circuitry 121, is also referred to as a collector.

The static magnetic field magnet 101 is a magnet formed in a hollow, approximately cylindrical shape. The static magnetic field magnet 101 is not necessarily in an approximately cylindrical shape, and may be formed in an open shape. The static magnetic field magnet 101 generates a uniform static magnetic field in an inner space. For example, a superconductive magnet or the like is used as the static magnetic field magnet 101.

The gradient magnetic field coil 103 is a coil formed in a hollow, cylindrical shape. The gradient magnetic field coil 103 is arranged inside the static magnetic field magnet 101. The gradient magnetic field coil 103 is formed by combining three coils respectively corresponding to the X, Y, and Z axes which are orthogonal to one another. The Z-axis direction is the same as the direction of the static magnetic field. In addition, the Y-axis direction is a vertical direction, and the X-axis direction is a direction perpendicular to each of the Z axis and the Y axis. The three coils in the gradient coil 103 are individually supplied with an electric current from the gradient magnetic field power supply 105, and generate a gradient magnetic field whose magnetic field intensity changes along each of the X, Y, and Z axes.

The gradient magnetic field of each of the X, Y, and Z axes generated by the gradient magnetic field coil 103 forms, for example, a gradient magnetic field for frequency encoding (also referred to as a readout gradient magnetic field), a gradient magnetic field for phase encoding, and a gradient magnetic field for slice selection. The gradient magnetic field for slice selection is used to determine an imaging cross section. The gradient magnetic field for phase encoding is used to change the phase of an MR signal in accordance with a spatial position. The gradient magnetic field for frequency encoding is used to change the frequency of an MR signal in accordance with a spatial position.

The gradient magnetic field power supply 105 is a power supply device that supplies an electric current to the gradient magnetic field coil 103 under control of the sequence control circuitry 121.

The bed 107 is a device with a top plate 1071 on which a subject P is placed. The bed 107 inserts the top plate 1071 on which the subject P is placed into a bore 111, under control of the bed control circuitry 109. The bed 107 is, for example, installed in an examination room where the magnetic resonance imaging apparatus 100 is installed, in such a manner that the longitudinal axis of the bed 107 is parallel to the center axis of the static magnetic field magnet 101.

The bed control circuitry 109 is circuitry that controls the bed 107, and drives the bed 107 in response to an operator's instruction via the interface 125 to move the top plate 1071 in a longitudinal direction and a vertical direction.

The transmitter coil 115 is an RF coil arranged inside the gradient magnetic field coil 103. The transmitter coil 115 is supplied with a radio frequency (RF) pulse from the transmission circuitry 113, and generates a transmit RF wave corresponding to a high-frequency magnetic field. The transmitter coil 115 is, for example, a whole body coil (hereinafter referred to as the WBC). The WBC may be used as a transmitter/receiver coil. A cylindrical RF shield is installed between the WB coil and the gradient magnetic field coil 103 to magnetically separate these coils.

The transmission circuitry 113 supplies an RF pulse corresponding to a Larmor frequency, etc. to the transmitter coil 115 under control of the sequence control circuitry 121.

The receiver coil 117 is an RF coil arranged inside the gradient magnetic field coil 103. The receiver coil 117 receives an MR signal emitted from the subject P, caused by a high-frequency magnetic field. The receiver coil 117 outputs the received MR signal to the reception circuitry 119. The receiver coil 117 is a coil array including, for example, one or more, typically, a plurality of coil elements. The receiver coil 117 is, for example, a phased array coil.

The reception circuitry 119 generates a digital MR signal, which is digitized complex data, based on the MR signal output from the receiver coil 117, under control of the sequence control circuitry 121. Specifically, the reception circuitry 119 performs various signal processing on the MR signal output from the receiver coil 117, and then executes analog-to-digital (A/D) conversion on the data on which the various signal processing is performed. The reception circuitry 119 samples the A/D-converted data. The reception circuitry 119 thereby generates a digital MR signal (hereinafter referred to as the MR data). The reception circuitry 119 outputs the generated MR data to the sequence control circuitry 121.

The sequence control circuitry 121 controls the gradient magnetic field power supply 105, the transmission circuitry 113, the reception circuitry 119, etc. in accordance with an examination protocol output from the processing circuitry 131, and executes imaging on the subject P. For example, the spoiled GRE imaging and the FISP imaging shown in FIG. 4 or 5 are repeated alternately. The spoiled GRE imaging and the FISP imaging that change the flip angle for each shot are repeated alternately.

An examination protocol has various pulse sequences in accordance with the examination. The examination protocol defines a magnitude of a current supplied from the gradient magnetic field power supply 105 to the gradient magnetic field coil 103, a timing of supply of the current from the gradient magnetic field power supply 105 to the gradient magnetic field coil 103, a magnitude of an RF pulse supplied from the transmission circuitry 113 to the transmitter coil 115, a timing of supply of the RF pulse from the transmission circuitry 113 to the transmitter coil 115, a timing of reception of an MR signal at the receiver coil 117, etc.

The bus 123 is a transmission path for transmitting data between the interface 125, the display 127, the storage 129, and the processing circuitry 131. To the bus 123, various biological signal measuring equipment, an external storage, various modalities, etc. may be connected as appropriate via a network, etc. For example, an electrocardiograph (not shown) is connected to the bus as biological signal measuring equipment.

The interface 125 includes a circuit that receives various instructions and information inputs from an operator. The interface 125 includes, for example, a circuit related to a pointing device such as a mouse or an input device such as a keyboard. The circuit included in the interface 125 is not limited to a circuit related to a physical operational component, such as a mouse or a keyboard. For example, the interface 125 may include an electrical signal processing circuit that receives an electrical signal corresponding to an input operation from an external input device provided separately from the magnetic resonance imaging apparatus 100 and outputs the received electrical signal to various circuits.

The display 127 displays various magnetic resonance images (MR images) generated by the image generation function, and various information related to imaging and image processing, under control of a system control function 1311 in the processing circuitry 131. The display 127 is, for example, a display device such as a CRT display, a liquid crystal display, an organic EL display, an LED display, a plasma display, or any other display or monitor known in this technical field.

The storage 129 stores MR data with which k-space is filled via an image generation function 1313, image data generated by the image generation function 1313, etc. The storage 129 stores various examination protocols, an imaging condition including a plurality of imaging parameters that define the examination protocols, etc. The storage 129 stores programs corresponding to various functions that are executed by the processing circuitry 131. The storage 129 is, for example, a semiconductor memory element, such as a random access memory (RAM) and a flash memory, a hard disk drive, a solid state drive, or an optical disk. The storage 129 may be a drive that reads and writes various types of information from and to a CD-ROM drive, a DVD drive, or a portable storage medium such as a flash memory.

The processing circuitry 131 has, as hardware resources, a processor, a memory such as a read-only memory (ROM) and a RAM, etc. (not shown), and collectively controls the magnetic resonance imaging apparatus 100. The processing circuitry 131 has the system control function 1311, the image generation function 1313, the acquisition function 21, the generation function 22, the reconstruction function 23, and the optimization function 24. Since the acquisition function 21, generation function 22, reconstruction function 23, and optimization function 24 are the same as the functions included in the processing circuitry 2 of the medical data processing apparatus 1 according to the above-described embodiment, descriptions thereof are omitted here.

The various functions of the processing circuitry 131 are stored in the storage 129 in the form of programs executable by a computer. The processing circuitry 131 is a processor that reads the programs corresponding to these various functions from the storage 129 and executes the programs to realize the functions corresponding to the programs. In other words, the processing circuitry 131 that has read each program is equipped with the plurality of functions shown in the processing circuitry 131 of FIG. 17.

FIG. 17 illustrates the case in which the various functions are realized in single processing circuitry 131; however, the processing circuitry 131 may be constituted by a combination of a plurality of independent processors, and the functions may be realized by the processors respectively executing the programs. In other words, each of the above-described functions may be formed as a program, and single processing circuitry may execute each program, or a specific function may be implemented in exclusive, independent program-execution circuitry.

The term "processor" used in the above description refers to, for example, circuitry such as a central processing unit (CPU), a graphics processing unit (GPU), an application specific integrated circuit (ASIC), a programmable logic device (e.g., a simple programmable logic device (SPLD)), a complex programmable logic device (CPLD), or a field programmable gate array (FPGA).

If the processor is a CPU, the processor realizes its function by reading and executing the program stored in storage circuitry. On the other hand, if the processor is an ASIC, that function is directly incorporated in a circuit of the processor as a logic circuit, instead of a program being stored in the storage circuitry. Similarly, each of the bed control circuitry 109, the transmission circuitry 113, the reception circuitry 119, the sequence control circuitry 121, etc. is also formed as an electronic circuit, such as the above processor.

The processing circuitry 131, with the system control function 1311, controls the magnetic resonance imaging apparatus 100. Specifically, the processing circuitry 131 reads a system control program stored in the storage 129, loads it in the memory, and controls each circuit of the magnetic resonance imaging apparatus 100 in accordance with the loaded system control program. For example, the processing circuitry 131, with the system control function 1311, reads an examination protocol from the storage 129 based on an imaging condition input by the operator via the interface 125. The processing circuitry 131 may generate the examination protocol based on the imaging condition. The processing circuitry 131 transmits the examination protocol to the sequence control circuitry 121 to control imaging of the subject P.

The processing circuitry 131, with the system control function 1311, controls the imaging so as to apply an excitation pulse in accordance with an excitation pulse sequence and apply a gradient magnetic field. After execution of the excitation pulse sequence, the processing circuitry 131, with the system control function 1311, collects an MR signal from the subject P in accordance with a data collection sequence, which is a pulse sequence for collecting various data, thereby generating MR data.

The processing circuitry 131, with the image generation function 1313, fills the MR data along a readout direction of k-space in accordance with an intensity of a readout gradient magnetic field. The processing circuitry 131 generates an MR image by executing a Fourier transform on the MR data with which the k-space is filled. For example, the processing circuitry 131 can generate an absolute value (magnitude) image from complex MR data. Also, the processing circuitry 131 can generate a phase image using real-part data and imaginary-part data in the complex MR data. The processing circuitry 131 outputs the MR images such as the absolute value image and the phase image to the display 127 and the storage 129.

According to the second embodiment described above, it is possible to generate a low-rank approximate value corresponding to full sampling from imaging data collected by executing spoiled GRE imaging and coherent GRE imaging. Thus, in the same manner as in the first embodiment, it is possible to provide high-speed and highly reliable quantitative values of various parameters and parameter maps.

According to at least one embodiment described above, high-speed and highly reliable estimation can be executed.

In addition, each function according to the embodiment can also be realized by installing a program for performing that processing on a computer such as a workstation and loading it in a memory. The program that causes the computer to execute the technique can be stored and distributed by means of a storage medium, such as a magnetic disc (a hard disc, etc.), an optical disc (CD-ROM, DVD, Blu-ray (registered trademark), etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical data processing apparatus comprising processing circuitry configured to:
   acquire a plurality of pieces of imaging data acquired by executing spoiled gradient echo imaging and coherent gradient echo imaging by using a plurality of flip angles;
   generate a low-rank approximate image set, which is a set of low-rank approximated images, from the imaging data; and
   reconstruct one or more parameter maps using the low-rank approximate image set and a multi-pool model related to water exchange in a biological tissue, the multi-pool model including plural free waters and bound water that performs magnetization exchange with the free waters.

2. The medical data processing apparatus according to claim 1, wherein the processing circuitry is configured to:
   generate a first sparse-sampling low-rank approximate image set by executing low-rank approximation on the imaging data; and
   infer a full-sampling low-rank approximate image set, as the low-rank approximate image set, from the first sparse-sampling low-rank approximate image set by using a first trained model, the first trained model being trained so that a second sparse-sampling low-rank approximate image set is input, a full-sampling low-rank approximate image set generated by executing low-rank approximation on fully sampled imaging data is output.

3. The medical data processing apparatus according to claim 2, wherein the processing circuitry is further configured to perform optimization processing by alternately repeating inference of a full-sampling low-rank approximate image using the first trained model and estimation of a full-sampling low-rank approximate image from the imaging data.

4. The medical data processing apparatus according to claim 3, wherein the processing circuitry is configured to perform the optimization processing by using an alternating direction method of multipliers (ADMM).

5. The medical data processing apparatus according to claim 2, wherein the processing circuitry is configured to:
   infer a quantitative value related to one or more parameters from the inferred full-sampling low-rank approximate image by using a second trained model, the second trained model being trained so that a full-sampling low-rank approximate image for training is input, a quantitative value related to one or more parameters is output; and
   generate the one or more parameter maps based on the inferred quantitative value related to the one or more parameters.

6. The medical data processing apparatus according to claim 2, wherein the processing circuitry is configured to calculate a T1 value and a T2 value from a full-sampling low-rank approximate image, based on a single-compartment analysis with a sequence different from an imaging sequence related to the spoiled gradient echo imaging and the coherent gradient echo imaging.

7. The medical data processing apparatus according to claim 1, wherein the processing circuitry is configured to generate N sparse-sampling low-rank approximate images by calculating a weight sum for each of N sets of weight coefficients, the weight sum being obtained by multiplying each of M imaging data by M weight coefficients in the each of the N sets, N being smaller than M.

8. The medical data processing apparatus according to claim 1, wherein the imaging data is data obtained by executing the spoiled gradient echo imaging and the coherent gradient echo imaging with a method for changing a magnetization transfer effect incorporated.

9. The medical data processing apparatus according to claim 8, wherein the method is to change a pulse width of an RF pulse.

10. The medical data processing apparatus according to claim 8, wherein the method is to apply an off-resonance MT pulse.

11. The medical data processing apparatus according to claim 10, wherein the method is to change an off-resonance frequency of the off-resonance MT pulse.

12. The medical data processing apparatus according to claim 1, wherein the processing circuitry is further configured to generate, from a full-sampling low-rank approximate image, one or more types of weight images with a sequence different from an imaging sequence related to the spoiled gradient echo imaging and the coherent gradient echo imaging.

13. The medical data processing apparatus according to claim 1, wherein the multi-pool model is a model in which parameters are reduced in number by providing restriction conditions on one or more of the parameters.

14. The medical data processing apparatus according to claim 1, wherein the processing circuitry is further configured to divide the imaging data into a plurality of regions and generate a low-rank approximate image set in each of the regions.

15. The medical data processing apparatus according to claim 1, wherein the processing circuitry is further configured to acquire the imaging data acquired by executing the spoiled gradient echo imaging and the coherent gradient echo imaging while changing a flip angle for each shot.

16. A medical data processing method comprising:
   acquiring a plurality of pieces of imaging data acquired by executing spoiled gradient echo imaging and coherent gradient echo imaging by using a plurality of flip angles;
   generating a low-rank approximate image set, which is a set of low-rank approximated images, from the imaging data; and
   reconstructing one or more parameter maps using the low-rank approximate image set and a multi-pool model related to water exchange in a biological tissue, the multi-pool model including plural free waters and bound water that performs magnetization exchange with the free waters.

17. A magnetic resonance imaging apparatus comprising processing circuitry configured to:
collect a plurality of pieces of imaging data by executing spoiled gradient echo imaging and coherent gradient echo imaging at a plurality of flip angles for a subject;
generate a low-rank approximate image set, which is a set of low-rank approximated images, from the imaging data; and
reconstruct one or more parameter maps using the low-rank approximate image set and a multi-pool model related to water exchange in a biological tissue, the multi-pool model including plural free waters and bound water that performs magnetization exchange with the free waters.

* * * * *